US012805821B2

(12) United States Patent
Ohishi

(10) Patent No.: US 12,805,821 B2
(45) Date of Patent: Nov. 24, 2026

(54) MEDICAL IMAGE PROCESSING APPARATUS, X-RAY DIAGNOSTIC APPARATUS, MEDICAL IMAGE PROCESSING METHOD AND X-RAY DIAGNOSTIC METHOD

(71) Applicant: Canon Kabushiki Kaisha, Tokyo (JP)

(72) Inventor: Satoru Ohishi, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 694 days.

(21) Appl. No.: 15/930,762

(22) Filed: May 13, 2020

(65) Prior Publication Data

US 2020/0268335 A1 Aug. 27, 2020

Related U.S. Application Data

(60) Division of application No. 14/871,252, filed on Sep. 30, 2015, now abandoned, which is a continuation of
(Continued)

(30) Foreign Application Priority Data

Apr. 1, 2013 (JP) ................................ 2013-076471

(51) Int. Cl.
*A61B 6/00* (2024.01)
*A61B 6/40* (2024.01)
(Continued)

(52) U.S. Cl.
CPC .............. *A61B 6/5217* (2013.01); *A61B 6/40* (2013.01); *A61B 6/42* (2013.01); *A61B 6/481* (2013.01);
(Continued)

(58) Field of Classification Search
CPC ........... A61B 6/5217; A61B 6/40; A61B 6/42; A61B 6/481; A61B 6/504; A61B 6/52; A61B 6/4225; A61B 6/4441; A61B 6/461
See application file for complete search history.

(56) References Cited

U.S. PATENT DOCUMENTS 4,633,307 A * 12/1986 Honda .................. A61B 6/481 378/98.12
7,596,255 B2 * 9/2009 Mathew ................ G06T 7/0012 715/974

(Continued)

FOREIGN PATENT DOCUMENTS

JP 4-682 1/1992
JP 2009-268693 11/2009
WO WO-2006051831 A1 * 5/2006 ............ G06T 11/10

OTHER PUBLICATIONS

Nicolas G. Rognin et al., Parametric Imaging for Characterizing Focal Liver Lesions in Contrast-Enhanced Ultrasound, IEEE Transactions on Ultrasonics, Ferroelectrics, and Frequency Control, vol. 57, No. 11, Nov. 2010 p. 2503-2511 (Year: 2010).*

(Continued)

*Primary Examiner* — Christopher Koharski
*Assistant Examiner* — Helene Bor
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry is configured to obtain time changes of concentrations of a contrast agent, based on at least X-ray contrast image data; generate a gray scale or a color scale by assigning a change in pixel value for at least one period, to a period shorter than a period from an initial time to an ending time of the time changes of the concentrations of the contrast agent; and generate blood vessel image data according to the
(Continued)

gray scale or the color scale. The blood vessel image data have pixel values corresponding to times at which the concentrations of the contrast agent become a specific condition.

20 Claims, 10 Drawing Sheets

Related U.S. Application Data application No. PCT/JP2014/058369, filed on Mar. 25, 2014.

(51) Int. Cl.
*A61B 6/42* (2024.01)
*A61B 6/46* (2024.01)
*A61B 6/50* (2024.01)

(52) U.S. Cl.
CPC ................ *A61B 6/504* (2013.01); *A61B 6/52* (2013.01); *A61B 6/4225* (2013.01); *A61B 6/4441* (2013.01); *A61B 6/461* (2013.01)

(56) References Cited

U.S. PATENT DOCUMENTS 8,050,474 B2 11/2011 Baumgart
8,064,667 B2 11/2011 Kawasaki et al.
8,929,632 B2 * 1/2015 Horz ...................... G16H 50/20 382/162
9,110,156 B2 * 8/2015 Kim ....................... G01N 29/44
2002/0091319 A1 * 7/2002 Moehring .............. A61B 8/463 600/454
2002/0103437 A1 * 8/2002 Jibiki .................. G01S 15/8988 600/454
2008/0232666 A1 * 9/2008 Rottger ................... G06T 15/08 382/131
2009/0110252 A1 * 4/2009 Baumgart ............... G06T 19/20 382/130
2009/0253986 A1 * 10/2009 Frinking ............. G01S 7/52074 600/431
2010/0067767 A1 * 3/2010 Arakita .................. A61B 6/504 382/131
2010/0094133 A1 * 4/2010 Yoshiara ................ A61B 8/469 600/458
2011/0208091 A1 * 8/2011 Butz .................... A61B 5/1519 600/583
2012/0177265 A1 * 7/2012 Yoshiara ................ A61B 5/055 382/128
2013/0077839 A1 3/2013 Horz et al.
2013/0116557 A1 * 5/2013 Yoshikawa .............. A61B 8/06 600/431
2014/0114185 A1 * 4/2014 Tolkowsky ............ A61B 6/504 600/431

OTHER PUBLICATIONS

English Translation of WO-2006051831-A1 (Year: 2006).*
International Search Report issued Apr. 22, 2014 in PCT/JP2014/058369 filed Mar. 3, 2014 (with English Translation of Categories of Cited Documents).
Written Opinion issued Apr. 22, 2014 in PCT/JP2014/058369 filed Mar. 3, 2014.
International Preliminary Report on Patentability issued Oct. 15, 2015 in corresponding PCT/JP2014/058369 filed on Mar. 25, 2014 (English translation only).
Japanese Office Action issued Jan. 10, 2017 in Patent Application No. 2013-076471.
Office Action issued Jul. 4, 2017 in Chinese Patent Application No. 201480019568.6 (with unedited computer generated English translation).
Second Office Action issued May 23, 2018 in Chinese Patent Application No. 201480019568.6.
Combined Chinese Office Action and Search Report issued Apr. 22, 2023, in corresponding Chinese Patent Application No. 201910149149.9 (with English Translation of Category of Cited Documents), 7 pages.
Chinese Office Action mailed on Apr. 22, 2023, issued in Chinese Patent Application No. 201910149149.9.
Chinese Office Action dated Jan. 30, 2024, issued in Chinese Patent Application No. 201910149149.9 (with English translation).
Chinese Office Action mailed on Apr. 22, 2023, issued in Chinese Patent Application No. 201910149149.9 (English translation).

* cited by examiner

MEDICAL IMAGE PROCESSING APPARATUS, X-RAY DIAGNOSTIC APPARATUS, MEDICAL IMAGE PROCESSING METHOD AND X-RAY DIAGNOSTIC METHOD

CROSS REFERENCES TO RELATED APPLICATIONS

This application is a divisional application of U.S. Ser. No. 14/871,252, filed on Sep. 30, 2015, which is a continuation of Application No. PCT/JP2014/58369, filed on Mar. 25, 2014, which is based upon and claims the benefit of priority from Japanese Patent Application No. 2013-076471 filed on Apr. 1, 2013; the entire contents of which are incorporated herein by reference.

FIELD

Embodiments described herein relate generally to a medical image processing apparatus, an X-ray diagnostic apparatus, a medical image processing method and an X-ray diagnostic method.

BACKGROUND

DSA (Digital Subtraction Angiography) is known as one of imaging methods for blood vessels in an X-ray diagnostic apparatus. DSA is the technology to generate subtraction image data between frames of X-ray image data before and after injecting a contrast agent into an object, for diagnosis. That is, X-ray image data are acquired before injecting a contrast agent as a mask image data for generating subtraction image data. On the other hand, X-ray contrast image data is acquired by injecting the contrast agent. Then, DSA image data is generated for diagnosis by subtraction processing between the X-ray contrast image data and the mask image data.

Such DSA image data can be generated as image data in which unnecessary anatomies in observation of a blood vessel are removed. That is, diagnostic image data in which blood vessels enhanced by a contrast agent are depicted selectively can be obtained. Consequently, images useful for diagnosis of a blood vessel can be displayed.

[Prior Technical Literature]

[Patent literature 1] U.S. Pat. No. 8,050,474 B2

Even in the case of acquiring DSA images which are typical as blood vessel images acquired by an X-ray diagnostic apparatus, precise blood vessel structures for a diagnosis may not be determined when a cerebral arteriovenous malformation, a dural arteriovenous fistula or the like is diagnosed. Specifically, it is often difficult to specify and distinguish blood vessels through which a contrast agent flows into a diseased part.

Thus, an object of the present invention is to provide a medical image processing apparatus, an X-ray diagnostic apparatus, a medical image processing method and an X-ray diagnostic method which can obtain precise blood vessel structures allowing blood vessels, through which a contrast agent flows into a diseased part, to be identified more clearly.

DETAILED DESCRIPTION

Figure 1:
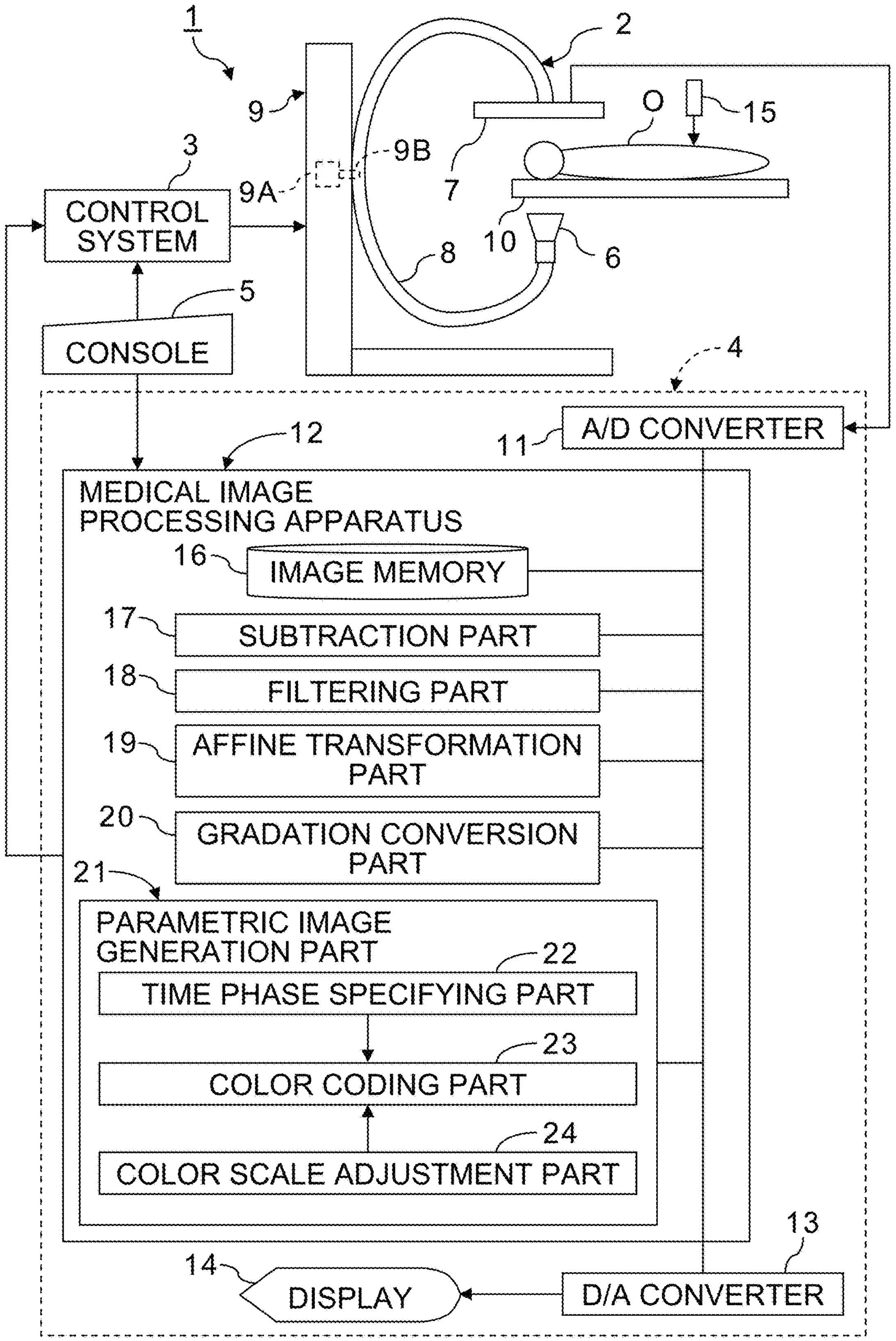
FIG. 1 is a configuration diagram of an X-ray diagnostic apparatus and a medical image processing apparatus according to an embodiment of the present invention.

In general, according to one embodiment, a medical image processing apparatus includes processing circuitry. The processing circuitry is configured to obtain time changes of concentrations of a contrast agent, based on at least X-ray contrast image data; generate a gray scale or a color scale by assigning a change in pixel value for at least one period, to a period shorter than a period from an initial time to an ending time of the time changes of the concentrations of the contrast agent; and generate blood vessel image data according to the gray scale or the color scale. The blood vessel image data have pixel values corresponding to times at which the concentrations of the contrast agent become a specific condition.

Further, according to one embodiment, a medical image processing apparatus includes processing circuitry. The processing circuitry is configured to obtain time changes in pixel value corresponding to a blood vessel, based on blood vessel image data acquired by an image diagnostic apparatus; generate a gray scale or a color scale by assigning a change in pixel value for at least one period, to a period shorter than a period from an initial time to an ending time of the time changes in the pixel value corresponding to the blood vessel; and generate blood vessel image data according to the gray scale or the color scale. The blood vessel image data have pixel values corresponding to times at which pixel values corresponding to the blood vessel become a specific condition.

Further, according to one embodiment, an X-ray diagnostic apparatus includes an X-ray tube, an X-ray detector and processing circuitry. The X-ray tube and the X-ray detector acquire at least X-ray contrast image data from an object. The processing circuitry is configured to obtain time changes of concentrations of a contrast agent, based on the at least X-ray contrast image data; generate a gray scale or a color scale by assigning a change in pixel value for at least one period, to a period shorter than a period from an initial time to an ending time of the time changes of the concentrations of the contrast agent; and generate blood vessel image data according to the gray scale or the color scale. The blood vessel image data have pixel values corresponding to times at which the concentrations of the contrast agent become a specific condition.

Further, according to one embodiment, a medical image processing method includes: obtaining time changes of concentrations of a contrast agent, based on at least X-ray contrast image data; generating a gray scale or a color scale by assigning a change in pixel value for at least one period, to a period shorter than a period from an initial time to an ending time of the time changes of the concentrations of the contrast agent; and generating blood vessel image data according to the gray scale or the color scale. The blood vessel image data have pixel values corresponding to times at which the concentrations of the contrast agent become a specific condition.

Further, according to one embodiment, an X-ray diagnostic method includes: acquiring at least X-ray contrast image data from an object; obtaining time changes of concentrations of a contrast agent, based on the at least X-ray contrast image data; generating a gray scale or a color scale by assigning a change in pixel value for at least one period, to a period shorter than a period from an initial time to an ending time of the time changes of the concentrations of the contrast agent; and generating blood vessel image data according to the gray scale or the color scale. The blood vessel image data have pixel values corresponding to times at which the concentrations of the contrast agent become a specific condition.

A medical image processing apparatus, an X-ray diagnostic apparatus, a medical image processing method and an X-ray diagnostic method according to embodiments of the present invention will be described with reference to the accompanying drawings.

FIG. 1 is a configuration diagram of an X-ray diagnostic apparatus and a medical image processing apparatus according to an embodiment of the present invention.

An X-ray diagnostic apparatus 1 includes an imaging system 2, a control system 3, a data processing system 4 and a console 5. The imaging system 2 has an X-ray tube 6, an X-ray detector 7, a C-shaped arm 8, a base 9 and a bed 10. In addition, the data processing system 4 has an A/D (analog to digital) converter 11, a medical image processing apparatus 12, a D/A (digital to analog) converter 13, and a display 14. Note that, the A/D converter 11 may be integrated with the X-ray detector 7.

The X-ray tube 6 and the X-ray detector 7 are settled at both ends of the C-shaped arm 8 so as to be mutually opposed at both sides of the interjacent bed 10. The C-shaped arm 8 is supported by the base 9. The base 9 has a motor 9A and a rotation mechanism 98. The motor 9A and the rotation mechanism 9B drive so as to rotate the X-ray tube 6 and the X-ray detector 7 fast into a desired position together with the C-shaped arm 8 like a propeller.

As the X-ray detector 7, a FPD (flat panel detector) or LL-TV (image intensifier TV) can be used. Furthermore, the output side of the X-ray detector 7 is connected with the A/D converter 11 of the data processing system 4.

The control system 3 drives and controls the imaging system 2 by outputting control signals to the respective elements consisting of the imaging system 2. The control system 3 is connected with the console 5 as an input circuit. Therefore, instruction of imaging conditions and the like to the control system 3 can be input from the console 5.

Then, the imaging system 2 is configured to expose X-rays toward an object O set on the bed 10 at mutually different angles sequentially from the rotatable X-ray tube 6 under control by the control system 3. In addition, the imaging system 2 is configured to acquire X-rays transmitting the object O from the plural directions sequentially as X-ray projection data by the X-ray detector 7. The X-ray projection data acquired by the X-ray detector 7 are output to the A/D converter 11 as X-ray image data.

Furthermore, a contrast agent injector 15 is provided in the vicinity of the object O set on the bed 10 in order to inject a contrast agent into the object O. Thus, X-ray contrast imaging of an object O can be performed by injecting a contrast agent from the contrast agent injector 15 into the object O. The contrast agent injector 15 can be also controlled by the control system 3.

Next, configurations and functions of the medical image processing apparatus 12 will be described.

The input side of the medical image processing apparatus 12 is connected with the output side of the A/D converter 11. Meanwhile, the display 14 is connected to the output side of the medical image processing apparatus 12 through the D/A converter 13. Moreover, the medical image processing apparatus 12 is connected with the console 5. Then, direction information required for data processing can be input into the medical image processing apparatus 12 by operation of the console 5.

Note that, aside from the medical image processing apparatus 12 built in the X-ray diagnostic apparatus 1 as illustrated in FIG. 1, a similar medical image processing apparatus as an independent system may be connected with the X-ray diagnostic apparatus 1 through a network.

The medical image processing apparatus 12 includes an image memory 16, a subtraction part 17, a filtering part 18, an affine transformation part 19, a gradation conversion part 20, and a parametric image generation part 21. The parametric image generation part 21 has a time phase specifying part 22, a color coding part 23, and a color scale adjustment part 24.

The medical image processing apparatus 12 having such functions can be configured by a computer reading a medical image processing program. That is, processing circuitry may be used to configure the medical image processing apparatus 12.

The image memory 16 is a storage circuit for storing X-ray image data acquired by the imaging system 2. Therefore, when non-contrast X-ray imaging has been performed, non-contrast X-ray image data is stored in the image memory 16. Meanwhile, when X-ray imaging has been performed with injecting a contrast agent into an object O, X-ray contrast image data is stored in the image memory 16.

The subtraction part 17 has a function to generate time series DSA image data, depicting contrast-enhanced blood vessels, by subtraction processing between non-contrast X-ray image data read from the image memory 16 and time series X-ray contrast image data.

The filtering part 18 has a function to perform desired filter processing, such as a high-pass filtering, a low-pass filtering, or a smoothing filtering, of arbitrary data.

The affine transformation part 19 has a function to perform affine transformation processing, such as a scaling, a rotation movement, and a parallel translation, of X-ray image data, according to direction information input from the console 5.

The gradation conversion part 20 has a function to perform gradation conversion of X-ray image data by referring to an LUT (Look Up Table).

The parametric image generation part 21 has a function to acquire time changes in concentration of a contrast agent based on time series DSA image data or time series X-ray contrast image data and a function to generate parametric image data, having pixel values corresponding to times at which the concentrations of the contrast agent become a specific condition, as blood vessel image data.

For that purpose, the time phase specifying part 22 has a function to specify time phases, at which concentrations of the contrast agent become a specific condition, based on profiles indicating time changes in the concentrations of the contrast agent. Moreover, the color coding part 23 has a function to assign colors corresponding to time phases specified by the time phase specifying part 22. The color scale adjustment part 24 has a function to determine a color scale used for color coding in the color coding part 23.

The specific condition for assigning colors can be determined, according to diagnostic purposes, to concentrations of a contrast agent corresponding to time points when the contrast agent has flowed in or arrived at a focused blood vessel, concentrations of a contrast agent corresponding to time points when the contrast agent has flowed out from a focused blood vessel contrarily, or the like. For example, a time defining the specific condition can be a time when a concentration of a contrast agent becomes the maximum value, a predetermined ratio of the maximum value, or a threshold value.

Figure 2:
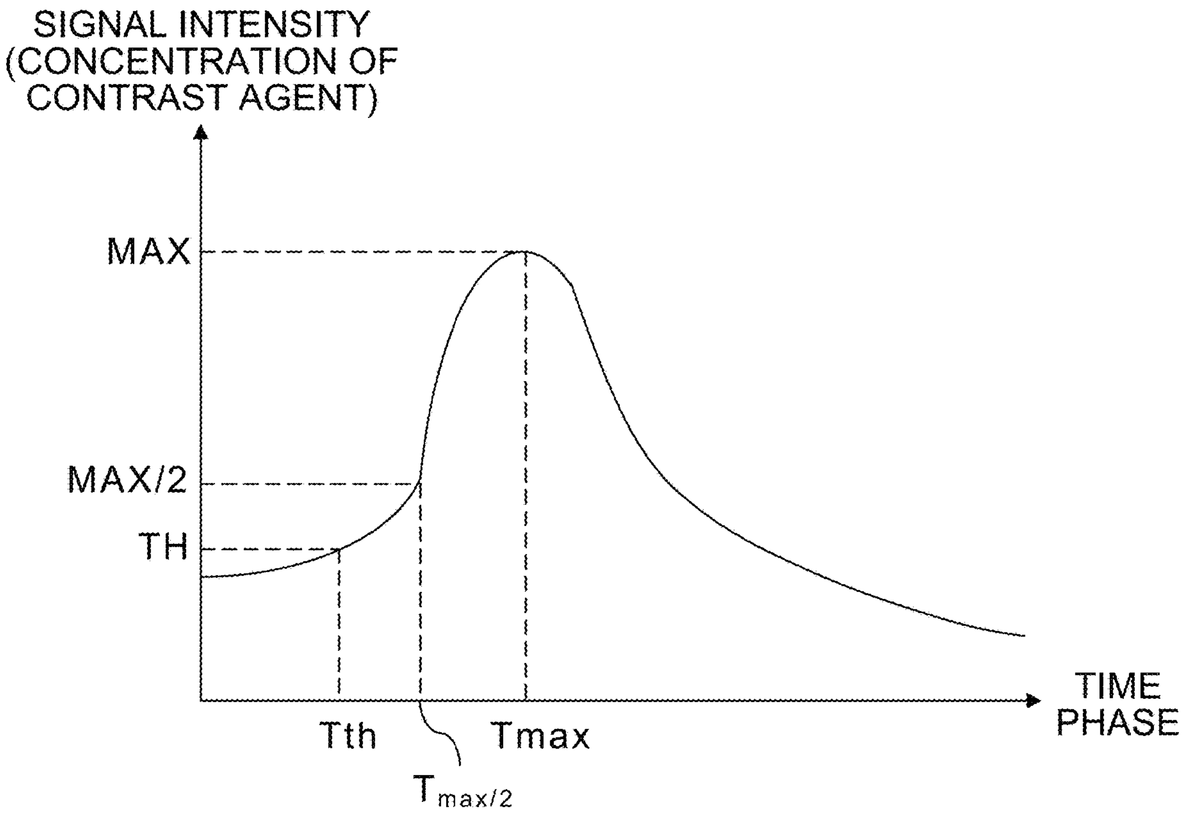
FIG. 2 shows a graph for explaining a method of identifying an inflow time or an arrival time of a contrast agent to a blood vessel based on a concentration profile of the contrast agent.

FIG. 2 shows a graph for explaining a method of identifying an inflow time or an arrival time of a contrast agent to a blood vessel based on a concentration profile of the contrast agent.

In FIG. 2, the horizontal axis shows the time phase direction while the vertical axis shows intensities of image signals, of DSA image data or contrast image data, representing concentrations of a contrast agent. As shown in FIG. 2, a profile in concentration change of the contrast agent can be obtained as a curve, showing signal intensities changing in time, by focusing a pixel corresponding to a blood vessel region of the time series DSA image data or contrast image data.

A typical concentration change profile becomes a curve of which the value increases gradually with the inflow of a contrast agent and decreases gradually with the outflow of the contrast agent. Therefore, when a threshold value TH for detecting a rising up of the curve is set for values of the concentration change profile, it becomes possible to identify a time phase at a start of contrast agent inflow into a focused blood vessel as a time phase Tth when the concentration of the contrast agent has reached the threshold value TH.

However, in a case that noises are large, the time phase at the start of a contrast agent inflow may be identified incorrectly. For this reason, a predetermined ratio within the range of 5% to 10% of the maximum value in a concentration profile of a contrast agent may be used for the threshold value so that influences of noises can be suppressed. Alternatively, a time phase Tmax at which a concentration of a contrast agent has reached the maximum value MAX or a time phase $T_{max/2}$ at which a concentration of a contrast agent has reached 50% of the maximum value MAX may be detected, from a concentration profile, as a time phase when the contrast agent has arrived at a blood vessel, as shown in FIG. 2. Hereinafter, an example case that an arrival time phase of a contrast agent is identified will be mainly described.

When the specification of a time phase, based on a concentration profile of a contrast agent, as shown in FIG. 2, is performed to each required pixel, and colors according to the specified time phases are assigned, parametric image data in which each blood vessel has been depicted in colors according to arrival times of the contrast agent or the like can be generated.

Note that, a time change in concentration of a contrast agent at each pixel representative of several pixels may be obtained by running average processing. That is, a matrix size of image data whose concentration of a contrast agent should be obtained can be minified with smoothing processing. Moreover, concentration changes of a contrast agent may be obtained based on image data whose noises have been removed by low-pass filter processing. These processing also can be said as running average processing or low-pass filtering processing of concentration profiles of a contrast agent in a spatial direction.

The running average processing or the low-pass filtering processing can also be performed not only in spatial directions but also in a time direction. In the case that the running average processing or the low-pass filtering processing is performed in the time direction, the processing is performed to concentration profiles of a contrast agent in the time direction.

Therefore, parametric image data can be generated based on time changes in concentration of a contrast agent after noise suppression processing in at least one of the time direction and spatial directions. Moreover, parametric image data can be generated based on time changes in concentration of a contrast agent after low-pass filtering processing in at least one of the time direction and spatial directions. Thereby, smooth parametric image data from which the noises have been dramatically suppressed can be generated.

Moreover, parametric image data can also be generated based on time changes, in concentration of a contrast agent, each having a data interval shorter than a sampling interval of the concentrations of the contrast agent corresponding to an imaging interval of X-ray contrast image data. A time change, in a concentration of a contrast agent, which has a data interval shorter than a sampling interval of the concentration of the contrast agent, can be obtained by arbitrary processing, such as interpolation processing, curve fitting processing using a specific function, or gravity center calculation processing. Thereby, it becomes possible to identify an arrival time of a contrast agent or the like at each pixel with a higher precision. In particular, it is more effective in a case that at least one of running average processing and low-pass filtering processing is performed.

Figure 3:
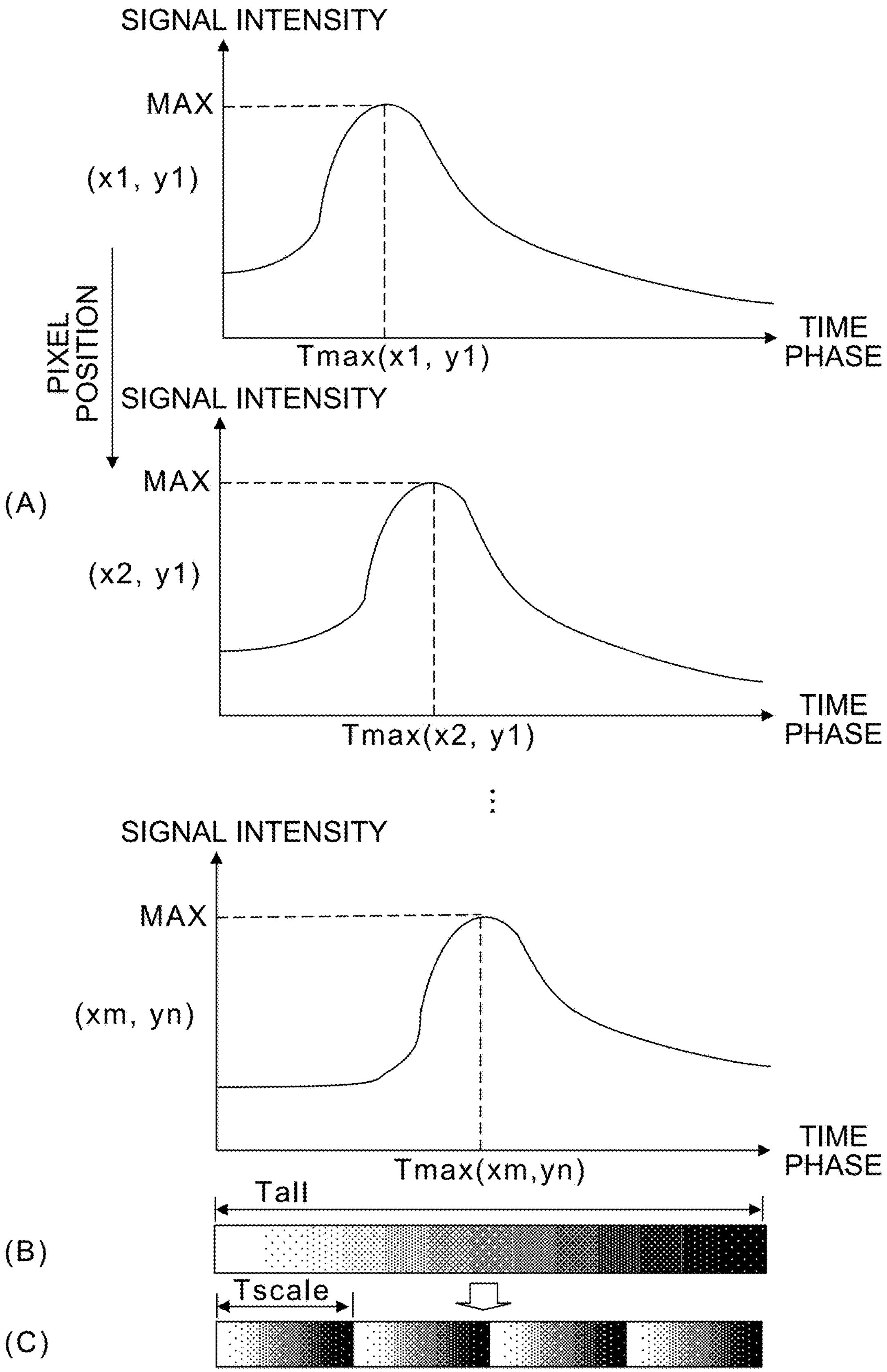
FIG. 3 shows the first example of color scale assigned to time phases corresponding to the maximum values of concentration profiles of a contrast agent.

FIG. 3 shows the first example of color scale assigned to time phases corresponding to the maximum values of concentration profiles of a contrast agent.

(A) of FIG. 3 shows concentration profiles of a contrast agent at two dimensional positions (xi, yj) (i=1, 2, 3, . . . , m; j=1, 2, 3, . . . , n) and arrival time phases Tmax (xi, yj) of the contrast agent specified based on the maximum values MAXs of the concentration profiles. The contrast agent arrives at a position, which is close to an injection position of the contrast agent, relatively early. Therefore, specified time phases are also relatively early. On the other hand, the contrast agent arrives at a position, which is away from the injection position of the contrast agent, relatively late. Therefore, specified time phases are also relatively late.

(B) of FIG. 3 shows an example of color scale assigned to the specified time phases as shown in (A) of FIG. 3. As shown in (B) of FIG. 3, a color scale can be generated by assigning a change in color pixel value for one period, consisting of R value, B value and G value, to a period Tall from the initial time to the ending time of time changes in concentrations of a contrast agent obtained as the concentration profiles. That is, a color scale can be generated by assigning a continuous color phase change for one period to the period Tall from the initial time to the ending time of time change in concentration of a contrast agent.

According to the color scale as shown in (B) of FIG. 3, a two dimensional time phase map showing arrival time phases of a contrast agent can be color coded. Then, parametric image data in which blood vessels have been depicted by different colors according to arrival time phases of a contrast agent can be generated.

However, when a difference in the arrival time phases Tmax (xi, yj) of a contrast agent between the pixel positions (xi, yj) is small relatively to a range of the color scale, as shown in (A) of FIG. 3, a difference in color between the pixel positions (xi, yj) becomes also small. Therefore, it may become difficult to distinguish small difference of time by the difference in color.

In particular, when X-ray imaging is performed for the purpose of diagnosing a dural arteriovenous fistula or a cerebral arteriovenous malformation, it is important to observe blood flows between arteries and veins. Therefore, it is often necessary to distinguish blood vessels having small differences in arrival times of a contrast agent.

Thus, a color scale can be changed in the color scale adjustment part 24 so that even blood vessels between which differences in arrival times of a contrast agent are small can be distinguished as differences in color. (C) of FIG. 3 shows an example of generating a color scale by assigning the continuous color phase change for one period multiple times to the period Tall, from the initial time to the ending time of time changes in concentrations of a contrast agent, as changes in pixel values. That is, a color scale in which a continuous color phase change is repeated periodically can be generated.

Such a color scale generated as described above can assign a change in pixel value, longer than the change in pixel value for one period, to the period Tall from the initial time to the ending time of time changes in concentrations of a contrast agent. Note that, although the example of generating a color scale by assigning the change in pixel value for one period multiple times has been shown in (C) of FIG. 3, a color scale in which the whole change in pixel value is not an integral multiple of the change in pixel value for one period may also be generated.

The color scale as shown in (C) of FIG. 3 can be generated by designating a pixel value corresponding to the initial time phase of concentration profiles, a period Tscale of a change in pixel value, and the initial pixel value in the period Tscale, with an operation of the console 5. Thereby, it is possible to generate a color scale in which the change in pixel value for one period is repeated according to the designated initial pixel value and the designated period Tscale. Then, the colors can be arranged in each period Tscale similarly to the color scheme as shown in (B) of FIG. 3. Specifically, a color scale in which a color phase showing the maximum value changes among red, green and blue in one period Tscale can be generated.

Figure 4:
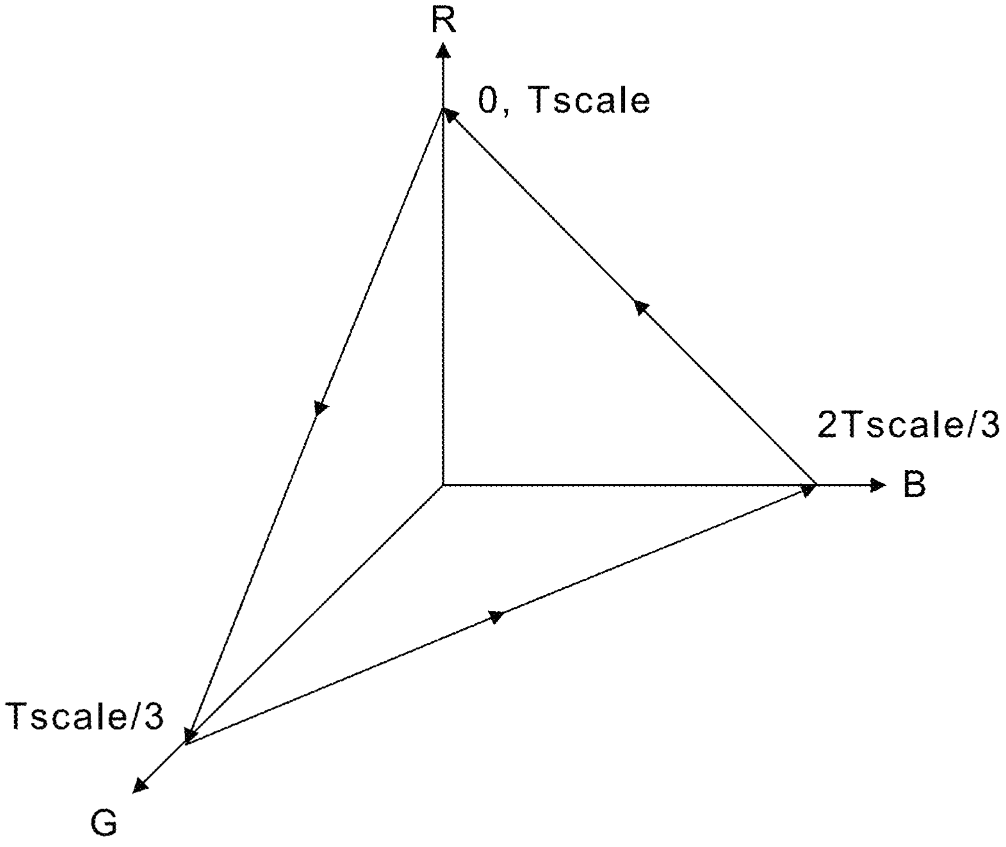
FIG. 4 shows an example of color scheme in the color scale shown in (C) of FIG. 3.

FIG. 4 shows an example of color scheme in the color scale shown in (C) of FIG. 3.

The three orthogonal axes in FIG. 4 represent R values, G values, and B values, respectively. The R value, G value, and B value corresponding to each time phase in the period Tscale can be determined along the sides of the color triangle, whose vertexes are the maximum value of the R values, the maximum value of the G values, and the maximum value of the B values, as shown in FIG. 4. Specifically, the colors can be arranged so that the G value and the B value become zero and the R value becomes the maximum value when the relative time is zero or Tscale, the R value and the B value become zero and the G value becomes the maximum value when the relative time is Tscale/3, and the R value and the G value become zero and the B value becomes the maximum value when the relative time is 2Tscale/3.

When such a color scheme is performed, parametric image data can be generated so that the color changes from red to blue through green, and then returns to red again according to the time phase. Note that, the colors between red, green, and blue can be assigned to time phases so that the R value, the G value, and the B value change linearly, for example. Alternatively, the R values, the G values, and the B values may also be assigned to time phases so that the angle of a line segment, which connects the center of the color triangle with a point on the sides, changes linearly.

When parametric image data are generated according to a color scale generated by such a color scheme, blood vessels can be distinguished as a difference in colors even when differences in arrival times of a contrast agent are small. That is, arrival times of a contrast agent can be understood in detail.

Note that, the most visible color is red. Therefore, as exemplified in FIG. 4, setting the color of an initial time phase, which corresponds to the earliest arrival time of a contrast agent, to red leads to an improvement of visibility. That is, it is effective to set a color value, corresponding to the initial time phase of a color scale, to the maximum value of the R value. Moreover, as another example, it is also useful to adjust the initial time phase so that a focused time phase becomes red.

Figure 5:
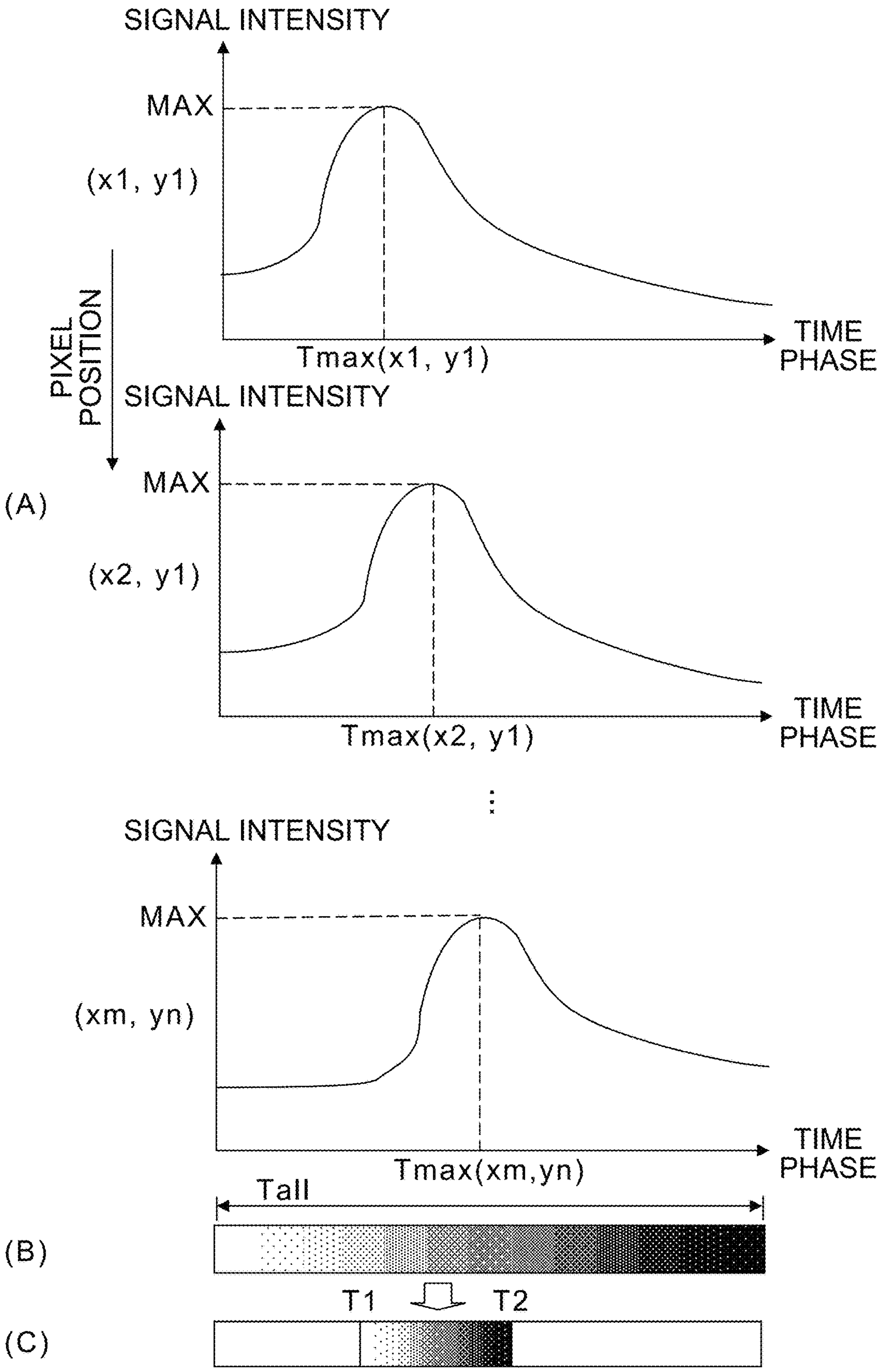
FIG. 5 shows the second example of color scale assigned to time phases corresponding to the maximum values of concentration profiles of a contrast agent.

FIG. 5 shows the second example of color scale assigned to time phases corresponding to the maximum values of concentration profiles of a contrast agent.

(A) of FIG. 5 shows concentration profiles of a contrast agent at two dimensional positions (xi, yj) (i=1, 2, 3, . . . , m; j=1, 2, 3, . . . , n) and arrival time phases Tmax (xi, yj) of the contrast agent specified based on the maximum values MAXs of the concentration profiles, similarly to (A) of FIG. 3.

Then, the color scale as shown in (B) of FIG. 5, in which a change in color pixel value is assigned to the period Tall from the initial time to the ending time of time changes in concentrations of a contrast agent, can be changed into the color scale shown in (C) of FIG. 5. The color scale shown in (C) of FIG. 5 is generated by assigning the continuous color phase change for one period, as a change in pixel value, to a designated period. The period to which the change in pixel value is assigned can be determined by designating a starting time phase T1 and an ending time phase T2. The starting time phase T1 and the ending time phase T2 can be designated by selecting corresponding images respectively from time series X-ray contrast images or time series DSA images.

Note that, a color scale can also be generated by assigning a change in pixel value, such as a change in pixel value for multiple periods as shown in (C) of FIG. 3, longer than one period, to the designated period as shown in (C) of FIG. 5. That is, a color scale can be generated by assigning a change in pixel value for at least one period, to a designated period.

Figure 6:
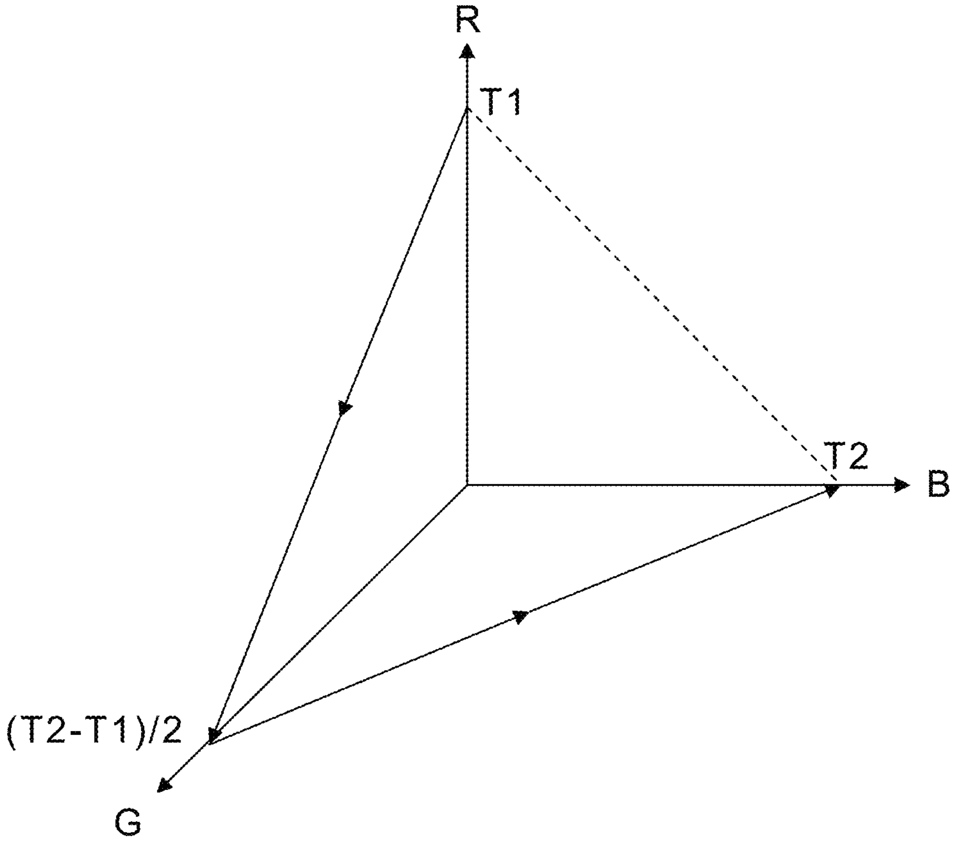
FIG. 6 shows an example of color scheme in the color scale shown in (C) of FIG. 5.

FIG. 6 shows an example of color scheme in the color scale shown in (C) of FIG. 5.

The three orthogonal axes in FIG. 6 represent R values, G values and B values, respectively. Similarly to FIG. 4, the R value, G value and B value corresponding to each time phase within a designated period can be determined along the sides of the color triangle. Specifically, the colors can be arranged so that the G value and the B value become zero and the R value becomes the maximum value at the starting time phase T1, the R value and the B value become zero and the G value becomes the maximum value at the middle time phase between the starting time phase T1 and the ending time phase T2, and the R value and the G value become zero and the B value becomes the maximum value at the ending time phase T2, similarly to an example shown in FIG. 4.

When the colors are arranged as shown in FIG. 6, a color scale in which a color phase showing the maximum value changes among red, green and blue between the starting time phase T1 and the ending time phase T2 can be generated. That is, a color scale whose color changes from red to blue through green within a designated period can be generated.

With regard to time phase other than a designated period, a pixel value pattern different from a change in pixel value in the designated period can be assigned. For example, color phases may be changed between the inside and the outside of the designated period. As a more specific example, a color scale can be generated so that the color phase changes from white to red at the time phases before the starting time phase T1 while the color phase changes from blue to white at the time phases after the ending time phase T2.

Furthermore, a transmittance different from that in a designated period can also be assigned to time phase other than the designated period. As a specific example, a color scale can be generated so that the transmittance changes from the maximum value to zero at the time phases before the starting time phase T1 while the transmittance changes from zero to the maximum value at the time phases after the ending time phase T2. That is, the transmittance may be changed in a predetermined range, in time phases outside the designated period. In this case, it is not necessary to change color values, such as R value and B value, outside the designated period.

As described above, at least one of pixel values, including R value, G value and B value, and the transmittance, in the time phase ranges outside the designated period can be changed from those within the designated period.

Each color scale after the change as shown in (C) of FIG. 3 and (C) of FIG. 5 can also be changed dynamically. Specifically, plural color scales can be generated by changing at least one of a phase and a period of change in pixel value of a color scale as shown in (C) of FIG. 3 or (C) of FIG. 5. Changing a phase of change in pixel value corresponds to shifting a color scale in the time phase direction. Meanwhile, changing a period of change in pixel value corresponds to expanding or contracting a color scale in the time phase direction.

Figure 7:
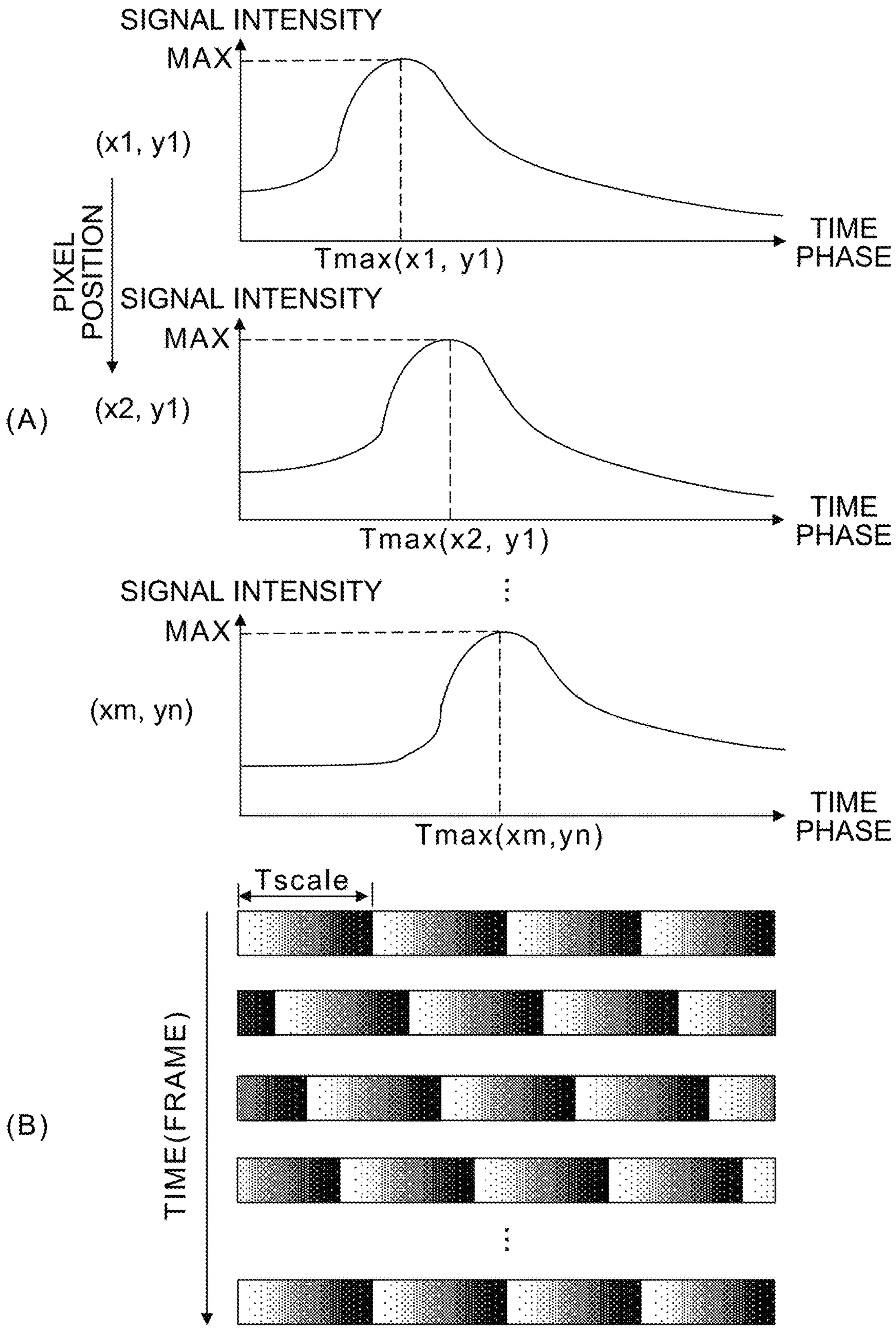
FIG. 7 shows an example of color scales generated for dynamically changing the color scale shown in (C) of FIG. 3.
Figure 8:
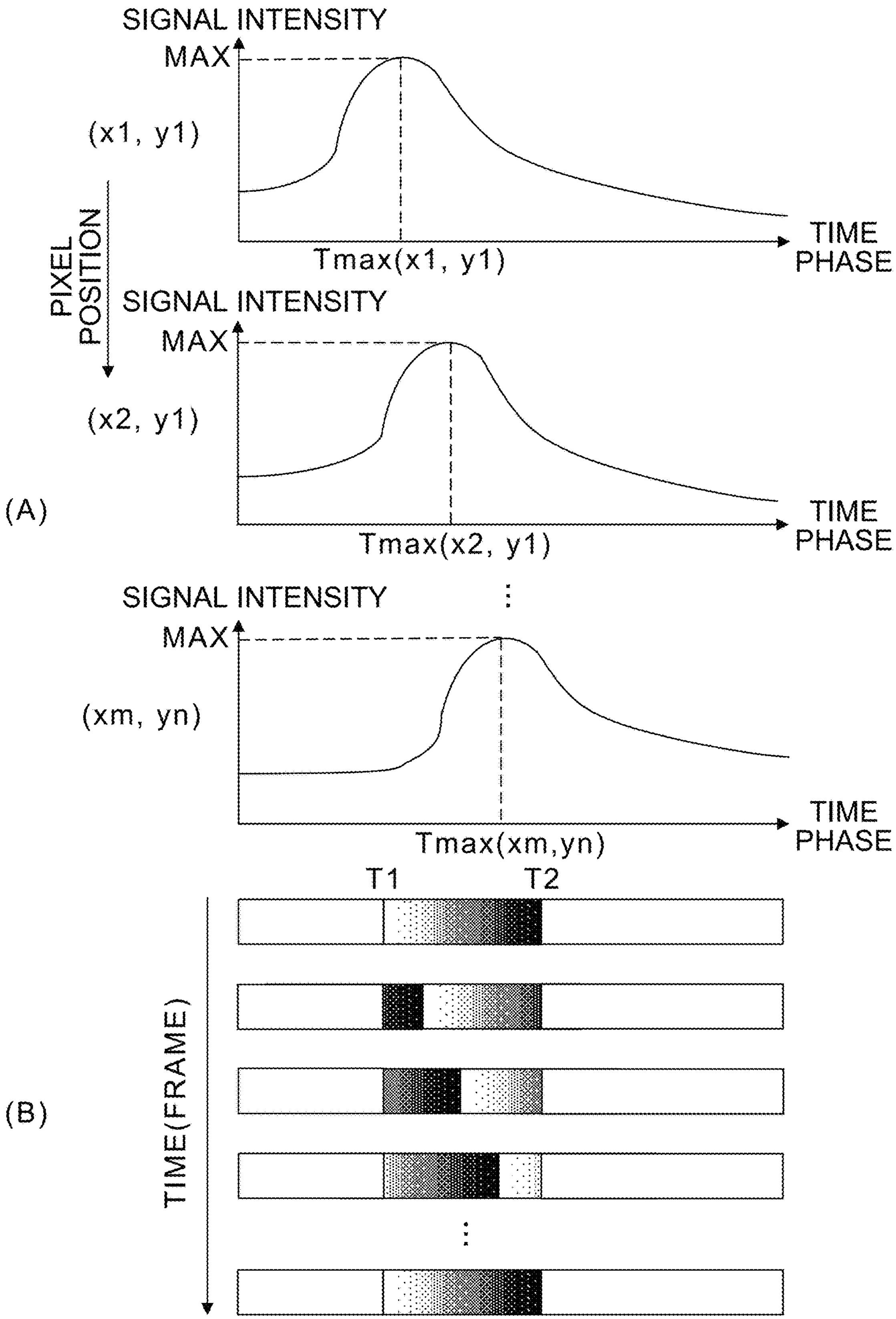
FIG. 8 shows an example of color scales generated for dynamically changing the color scale shown in (C) of FIG. 5.

FIG. 7 shows an example of color scales generated for dynamically changing the color scale shown in (C) of FIG. 3, and FIG. 8 shows an example of color scales generated for dynamically changing the color scale shown in (C) of FIG. 5.

Each of (A) of FIG. 7 and (A) of FIG. 8 shows concentration profiles of a contrast agent at two dimensional positions (xi, yj) (i=1, 2, 3, . . . , m; j=1, 2, 3, . . . , n) and arrival time phases Tmax(xi, yj) of the contrast agent specified based on the maximum values MAXs of the concentration profiles. Therefore, in each graph shown in (A) of FIG. 7 and (A) of FIG. 8, the horizontal axis shows time phases and the vertical axis shows relative signal intensities corresponding to concentrations of the contrast agent.

When a color scale, in which the change in pixel value for one period is assigned multiple times as shown in (C) of FIG. 3, is changed dynamically, what is necessary is to generate plural color scales by shifting the color scale shown in (C) of FIG. 3 in the change direction of the pixel value, as shown in (B) of FIG. 7. Similarly, when a color scale, in which the change in the pixel value for one period is assigned to the designated period as shown in (C) of FIG. 5, is changed dynamically, what is necessary is to generate plural color scales by shifting the color scale shown in (C) of FIG. 5 in the change direction of the pixel value, as shown in (B) of FIG. 8.

When the color coding of parametric image data is performed using color scales having different color schemes as described above, frames of parametric image data corresponding to the color scales are generated. Thus, it becomes possible to display the frames of generated parametric image data in the color scale direction as a moving image.

For example, in the example shown in (B) of FIG. 8, parametric image data can be generated, using the plural color scales, as a moving image in which changes in pixel values different from each other have been assigned to a period shorter than the period from the initial time to the ending time of time changes in concentrations of a contrast agent. Furthermore, plural color scales may be generated by changing not only a phase of change in pixel value but also a period of the change in pixel value, as described above.

As described above, blood vessel image data can be generated as a moving image according to plural color scales generated by changing at least one of a phase and a period of change in pixel value for at least one period. When parametric image data as blood vessel image data are displayed as a moving image, blood and a contrast agent can be displayed in color as if they flowed.

Note that, parametric image data can be generated, using the color scales, as a moving image having a frame interval different from that of X-ray contrast image data. That is, a frame interval for switching a color scale to a different color scale can be set to a desirable interval appropriate for a diagnosis, independently of the frame interval of the X-ray contrast image data. Therefore, a moving speed of the colors which simulate blood flows can be set to a desired speed.

Therefore, it becomes possible to understand flows of a contrast agent and blood more easily. In particular, human eyes have high visibility to red. Therefore, generating a moving image in which red moves during a focused period from the starting time phase T1 to the ending time phase T2 allows easy understanding of a blood flow dynamic state in a focused region.

As a specific example, when colors are changed in the designated period as shown in (B) of FIG. 8, a color corresponding to each time phase can be changed in time. In this case, a color changes among red, green and blue even at a same time phase. With regard to the outside of the designated period, colors at the starting time phase T1 and the ending time phase T2 can be gradually changed into white respectively, or the transmittances of colors can be changed.

Meanwhile, in the case of the color scale in which color values have been changed periodically as shown in (B) of FIG. 7, plural color scales can be generated by gradually changing the initial color value in each period, as mentioned above.

The color values including the R value, the G value and the B value can also be changed into values other than the maximum values. Specifically, when parametric image data are generated by the above-mentioned color scale, a brightness value at each pixel, at which a value of a concentration profile of a contrast agent has not become zero by low-pass filtering processing or the like, becomes the maximum value. That is, a brightness value at each pixel at which a contrast agent arrived becomes the maximum value, regardless of a concentration of the contrast agent.

Thus, brightness values of parametric image data can be changed so that concentrations of a contrast agent can be understood. In other words, parametric image data having brightness values according to concentrations of a contrast agent at a specific condition, such as the maximum values, can be generated as blood vessel image data.

Specifically, when the maximum R value, G value and B value before the change in brightness values are $R_0$, $G_0$ and $B_0$, respectively, the R value, G value and B value after the change in brightness values can be determined by multiplying each of the values $R_0$, $G_0$ and $B_0$ by a coefficient k, as shown in expression (1).

$$(R,G,B)=(kR_0,kG_0,kB_0) \quad (1)$$

In expression (1), the coefficient k is set to a value not less than zero and not more than one, corresponding to a concentration of a contrast agent. For example, the coefficient k can be determined by expression (2).

$$k=P(x,y)/P_0 \quad (2)$$

wherein P(x, y) represents a value, corresponding to a specific condition such as the maximum value, of a concentration profile of a contrast agent at a position (x, y), obtained as an image signal value of X-ray contrast image data or DSA image data, and $P_0$ represents a constant.

When the coefficient k is set by expression (2), the coefficient k becomes a value proportional to the value P(x, y) of a concentration profile of a contrast agent. Therefore, the brightness values (R, G, B) of parametric image data can also be brightness values each proportional to the value P(x, y) of a concentration profile of a contrast agent. Furthermore, brightness values at a pixel where a concentration of a contrast agent is a noise level and brightness values at a pixel where noises have actually occurred can be made small enough.

The constant $P_0$ can be set to the maximum value of the value P(x, y) of a concentration profile of a contrast agent in spatial directions, or an arbitrary value which has been determined empirically. Note that, when the constant $P_0$ is set to a value smaller than the maximum value of the value P(x, y) of a concentration profile of a contrast agent, the coefficient k may become a value larger than one, by the calculation of expression (2). In such a case, the coefficient k has only to be set to one.

Then, when a pixel value adjusted by expression (1) is assigned to each pixel position (x, y), parametric image data in which blood vessels have been depicted in colors and brightness according to arrival time phases and concentrations of a contrast agent can be generated. Note that, the adjustment of brightness values shown in expression (1) can be performed at the time of the color coding in the color coding part 23.

The parametric image data generated in the parametric image generation part 21 as described above can be displayed on the display 14, similarly to X-ray contrast image data or DSA image data. Furthermore, the parametric image data can be stored in the image memory 16 as necessary.

Figure 9:
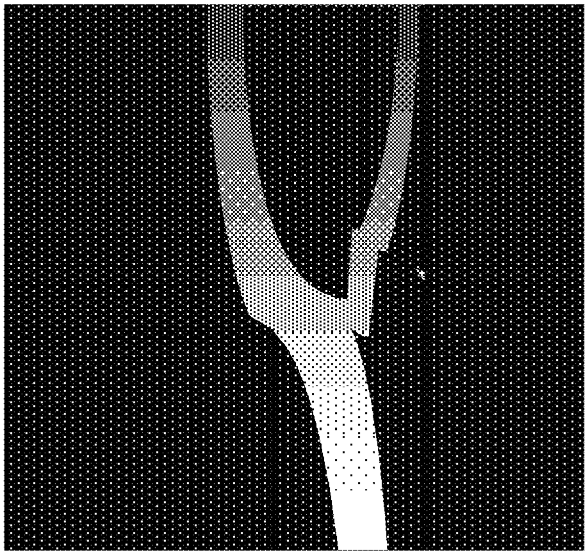
FIG. 9 shows an example of parametric image generated in the parametric image generation part shown in FIG. 1.

FIG. 9 shows an example of parametric image generated in the parametric image generation part 21 shown in FIG. 1.

In a parametric image, blood vessels into which a contrast agent has been injected are displayed in color while brightness values become zero in regions without the contrast agent, as shown in FIG. 9. Furthermore, the blood vessels are depicted as a region or regions where colors change according to arrival times of the contrast agent. Therefore, how blood and the contrast agent flow can be observed by colors.

In the X-ray diagnostic apparatus 1 and the medical image processing apparatus 12 having the functions and configurations as described above, the imaging system 2 and the control system 3 cooperating with each other function as an image acquisition system configured to acquire at least X-ray contrast image data from the object O. Furthermore, the time phase specifying part 22 and the color coding part 23, cooperating with each other, of the parametric image generation part 21 function as a blood vessel image generation part configured to obtain time changes in concentrations of a contrast agent based on at least X-ray contrast image data, and generate blood vessel image data, having pixel values corresponding to times at which the concentrations of the contrast agent become a specific condition, according to a color scale. In addition, the color scale adjustment part 24 of the parametric image generation part 21 functions as a pixel value scale generation part configured to generate a color scale by assigning a change in pixel value for at least one period, to a period shorter than the period from the initial time to the ending time of the time changes in the concentrations of the contrast agent.

Note that, the X-ray diagnostic apparatus 1 and the medical image processing apparatus 12 may be configured by other elements so long as similar functions as the image acquisition system, the blood vessel image generation part and the pixel value scale generation part are provided in the X-ray diagnostic apparatus 1 and the medical image processing apparatus 12. For example, the medical image processing apparatus 12 may be configured by installing a medical image processing program, which makes a computer function as the blood vessel image generation part and the pixel value scale generation part, to the computer. In that case, the medical image processing program can be recorded in an information recording medium to be distributed as a program product so that a general purpose computer can be used as the medical image processing apparatus 12.

Next, an operation and an action of the X-ray diagnostic apparatus 1 and the medical image processing apparatus 12 will be described.

Figure 10:
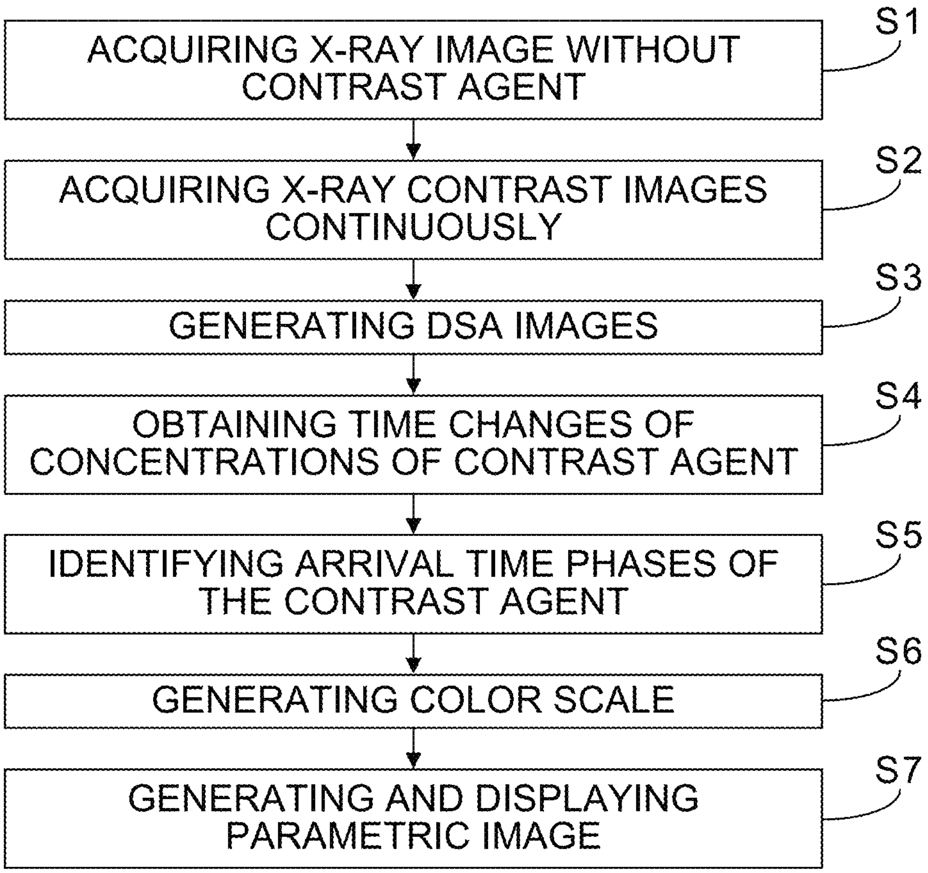
FIG. 10 is a flow chart which shows an operation of the X-ray diagnostic apparatus 1 shown in FIG. 1 and processing in the medical image processing apparatus 12 shown in FIG. 1.

FIG. 10 is a flow chart which shows an operation of the X-ray diagnostic apparatus 1 shown in FIG. 1 and processing in the medical image processing apparatus 12 shown in FIG. 1.

First, in step S1, X-ray image data are acquired without a contrast agent. Specifically, the imaging system 2 moves to a predetermined position and an X-ray is exposed from the X-ray tube 6 towards an object O set on the bed 10, under control by the control system 3. Then, the X-ray which has transmitted the object O is acquired as X-ray projection data by the X-ray detector 7. The X-ray projection data acquired by the X-ray detector 7 are output as X-ray image data to the medical image processing apparatus 12 through the A/D converter 11.

The X-ray image data may be acquired for one frame or multiple frames. When multiple frames of the X-ray image data are acquired and the addition average of the multiple frames of the X-ray image data is calculated in the filtering part 18, one frame of non-contrast X-ray image data whose noises have been reduced can be generated. Subsequently, the non-contrast X-ray image data acquired as mentioned above are stored in the image memory 16.

Next, in step S2, X-ray contrast image data are acquired continuously. For that purpose, the contrast agent injector 15 operates under a control by the control system 3, and a contrast agent is injected into the object O. Subsequently, after a preset time has passed from the start time of the contrast agent injection, the acquisition of the X-ray contrast image data starts. Then, the acquisition of the X-ray contrast image data is performed continuously in a predetermined period. Thereby, the time series X-ray contrast image data are stored sequentially in the image memory 16. The flow of acquiring the X-ray contrast image data is similar to the flow of acquiring non-contrast X-ray image data.

Next, in step S3, the DSA image data are generated by the subtraction part 17. More specifically, the time series DSA image data are generated sequentially by subtraction processing of the time series X-ray contrast image data using the non-contrast X-ray image data as mask image data. The generated time series DSA image data are stored sequentially in the image memory 16.

The time series X-ray contrast images or the time series DSA images can be displayed as live images in real time on the display 14. Furthermore, the time series X-ray contrast images or the time series DSA images can be also displayed on the display 14 after the X-ray imaging. When the DSA images are displayed afterward, the DSA image data can be generated by performing subtraction processing for only a time phase period designated by an operation of the console 5.

Next, in step S4, time changes in concentrations of the contrast agent are generated by the time phase specifying part 22. Specifically, the time series X-ray contrast image data or the time series DSA image data in a time phase period designated by operations of the console 5 are taken into the time phase specifying part 22. Then, a concentration profile showing a time change in concentration of the contrast agent as shown in (A) of FIG. 3 or (A) of FIG. 5 is generated for every pixel position in the time phase specifying part 22.

Note that, the filtering part 18 can perform one or both of low-pass filtering processing and running average processing in one or both of spatial directions and the time direction, as preprocessing or postprocessing of the generation of the concentration profiles of the contrast agent. Thereby, smooth concentration profiles, of the contrast agent, having less noises can be generated. In addition, concentration profiles of the contrast agent whose data intervals are shorter than sampling intervals can also be generated by interpolation processing, gravity center calculation, or curve fitting in the time phase specifying part 22.

Next, in step S5, arrival time phases of the contrast agent at the respective pixel positions are identified, by the time phase specifying part 22, based on the concentration profiles of the contrast agent. Specifically, the arrival time phase of the contrast agent can be identified for every pixel position by data processing, such as peak detection processing or threshold value processing, of the concentration profiles of the contrast agent.

Note that, after the time phases have been specified by the data processing such as peak detection processing or threshold value processing, continuous concentration profiles only in periods close to the specified time phases may be calculated by interpolation processing, gravity center calculation, or curve fitting. In that case, the true arrival time phases of the contrast agent are detected by data processing, such as peak detection processing or threshold value processing, of the acquired continuous concentration profiles, for the second time.

Next, in step S6, the color scale adjustment part 24 generates a color scale for color coding of a two dimensional map of the arrival time phases of the contrast agent acquired by the time phase specifying part 22. The color scale adjustment part 24 can generate not only a general color scale whose color phase changes continuously from the initial time phase to the last time phase at a constant rate of change as shown in (B) of FIG. 3 or (B) of FIG. 5 but also a color scale as shown in (C) of FIG. 3 or (C) of FIG. 5 by increasing a change rate in color phase of a normal color scale.

In a case of generating a color scale whose color phase changes continuously and periodically as shown in (C) of FIG. 3, the color scale can be generated by specifying the period Tscale, in which the color phase changes, and changing the color phase in each period Tscale, by an operation of the console 5. Alternatively, these necessary conditions may be previously set as default values. A color phase at the starting time phase in each period Tscale can be designated arbitrarily. Furthermore, when a color phase at the initial time phase of concentration changes of a contrast agent is not set to a color phase at the starting time phase in each period Tscale, the color phase at the initial time phase needs to be designated.

Meanwhile, in a case of generating a color scale having a continuous color phase change, within a designated time phase period, different from that outside the designated time phase period, as shown in (C) of FIG. 5, the color scale can be generated by designating the starting time phase T1 and the ending time phase T2 of the time phase period, to which the continuous color phase change is assigned, by operation of the console 5. The starting time phase T1 and the ending time phase T2 can be designated by selecting an image from the time series X-ray contrast images or the time series DSA images displayed on the display 14 by operation of the console 5.

Next, in step S7, the color coding part 23 performs color coding, of the two dimensional map of the arrival time phases of the contrast agent, based on the color scale generated by the color scale adjustment part 24. Specifically, an R value, a G value, and a B value corresponding to an arrival time phase of the contrast agent are assigned to each pixel, as pixel values, according to the color scale. Thereby, parametric image data are generated.

At this time, it is desirable to multiply each of the R value, the G value and the B value by a coefficient corresponding to a concentration of the contrast agent at the arrival time phase of the contrast agent. Thereby, parametric image data can be generated so that a brightness value at a pixel, at which a concentration of the contrast agent at the arrival time phase of the contrast agent is relatively high, is relatively high while a brightness value at a pixel, at which a concentration of the contrast agent at the arrival time phase of the contrast agent is relatively low, is relatively low.

Then, the parametric image generated as described above can be displayed on the display 14. The parametric image can also be displayed as a moving image by shifting, and/or expanding or contracting the color scale in the time phase direction. Consequently, observing the parametric image allows a user to recognize blood vessels into which a contrast agent flows. In particular, a color phase change in the color scale has been assigned to a short time phase period, and therefore, blood vessels in which arrival time phases of a contrast agent are near to each other can be easily distinguished by a difference in color.

That is, the X-ray diagnostic apparatus 1 and the medical image processing apparatus 12 as described above are configured to generate blood flow image data in color by color coding of specific time phases, such as arrival time phases, of a contrast agent with a color scale according to time phases and contract a continuous color phase change of the color scale in the time phase direction in order to improve time phase identification ability by color.

Therefore, according to the X-ray diagnostic apparatus 1 and the medical image processing apparatus 12, adjacent blood vessels can be easily distinguished as a difference in color phase even when a difference in inflow time phase, arrival time phase or outflow time phase of a contrast agent is small among the blood vessels.

In particular, it is important to observe a blood flow into a disease part between arteries and veins, in a diagnosis of a cerebral arteriovenous malformation or a dural arteriovenous fistula. Therefore, it is necessary to distinguish blood vessels into which a contrast agent flows. However, DSA images are displayed with a gray scale, and therefore, distinguishing contrast-enhanced blood vessels is difficult.

In contrast, the X-ray diagnostic apparatus 1 and the medical image processing apparatus 12 are configured to be able to set a period of a color phase change in a color scale to be short, according to a time phase difference which should be identified. Accordingly, colors change for every blood vessel even when a contrast agent flows into focused blood vessels almost simultaneously. Therefore, the blood vessels can be easily distinguished.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, an example case of generating blood vessel image data as color parametric image data, using a color scale, has been described in the embodiment described above. Alternatively, blood vessel image data may also be generated using a gray scale. Specifically, blood vessel image data having pixel values corresponding to times when concentrations of a contrast agent become a specific condition can be generated according to a gray scale or a color scale. Furthermore, a gray scale or a color scale can be generated by assigning a change in pixel value to a period shorter than the period from the initial time to the ending time of time changes in concentrations of a contrast agent.

When blood flow image data are generated using a gray scale, a continuous change in brightness value instead of a color phase change is to be assigned, as a change in pixel value, to a period shorter than the period from the initial time to the ending time of time changes in concentrations of a contrast agent. In that case, each brightness value can also be set to a value according to a concentration of the contrast agent by multiplying the brightness value by a coefficient k according to the concentration of the contrast agent.

Similarly, when blood flow image data are generated using a color scale, not only a continuous color phase change but a continuous change in brightness value can also be assigned as a change in pixel value as described above. In that case, each brightness value can also be set to a value according to a concentration of a contrast agent by multiplying the brightness value by a coefficient k according to the concentration of the contrast agent.

As described above, a change in pixel value assigned to a period shorter than the period from the initial time to the ending time of time changes in concentrations of a contrast agent may be a continuous color phase change, a continuous change in color brightness value, or a continuous change in gray brightness value.

In addition, the X-ray diagnostic apparatus 1 of which the X-ray tube 6 and the X-ray detector 7 have been fixed to the both ends of the C-shaped arm 8 has been exemplified in the embodiment described above. Similarly, an X-ray diagnostic apparatus having another structure can also generate parametric image data. Examples of an X-ray diagnostic apparatus having another structure include an X-ray diagnostic apparatus of which each of the X-ray tube 6 and the X-ray detector 7 is fixed to an independent arm, besides an X-ray diagnostic apparatus having multiple arms or an X-ray diagnostic apparatus including movement structures for moving arbitrary arms along axes in arbitrary directions, such as an arc axis or a straight axis. When each of the X-ray tube 6 and the X-ray detector 7 is fixed to an independent arm, it is practical to install driving structures, such as an expansion and contraction structure, a rotating structure, a joint structure and a link mechanism, on each of the first arm holding the X-ray tube 6 and the second arm holding the X-ray detector 7.

Further, an example case of generating parametric image data, which are blood vessel image data having pixel values corresponding to times at which concentrations of a contrast agent become a specific condition, based on X-ray contrast image data acquired by the X-ray diagnostic apparatus 1 has been described in the embodiment described above. However, parametric image data may also be generated based on blood vessel image data acquired by another image diagnostic apparatus (modality).

For example, in a case of using an MRI (magnetic resonance imaging) apparatus, MRA (magnetic resonance angiography) image data or non-contrast MRA image data can be acquired as contrast imaging or non-contrast imaging. In a case of acquiring contrast MRA image data, blood flow dynamic state information can be obtained as time changes in concentrations of a contrast agent. Meanwhile, in a case of acquiring non-contrast MRA image data, blood flow dynamic state information can be obtained as changes in image values enhanced by applying a spin labeling pulse, such as an ASL (arterial spin labeling) pulse, or an imaging method, such as a TOF (time of flight) method.

On the other hand, in a case of acquiring 4D (four dimensional) X-ray CT (computed tomography) contrast image data using an X-ray CT apparatus, blood flow dynamic state information can be obtained as time changes in concentrations of a contrast agent. Alternatively, an ultrasonic contrast scan using an ultrasonic diagnostic apparatus can also obtain blood flow dynamic state information as time changes in concentrations of a contrast agent.

Whether contrast blood vessel image data have been acquired by an image diagnostic apparatus or non-contrast blood vessel image data have been acquired, blood flows can be observed as time changes in pixel values corresponding to blood vessels.

Therefore, in a case of generating parametric image data based on blood vessel image data acquired by an arbitrary image diagnostic apparatus, a medical image processing apparatus has a blood vessel image generation part which is configured to obtain time changes in pixel values corresponding to blood vessels, based on the blood vessel image data acquired by the image diagnostic apparatus, and generate blood vessel image data, having pixel values corresponding to times at which the pixel values corresponding to the blood vessels become a specific condition, according to a gray scale or a color scale. Furthermore, the medical image processing apparatus has a pixel value scale generation part which is configured to generate the gray scale or the color scale, by assigning a change in pixel value for at least one period, to a period shorter than the period from the initial time to the ending time of the time changes in the pixel values corresponding to the blood vessels.

What is claimed is:

1. A medical image processing apparatus, comprising:

processing circuitry configured to:

determine, for each pixel of a plurality of pixels in a blood vessel region of two-dimensional projection image data of blood vessels in a head, the two-dimensional projection image data being X-ray contrast image data acquired in time series or digital subtraction angiography (DSA) image data acquired in the time series, a determined time at which a concentration of a contrast agent satisfies a specific condition;

generate a plurality of color scales that map a respective color to each of the determined times, the plurality of color scales being respectively different from each other and temporally offset relative to one another;

generate blood vessel image data from the determined times by assigning a color to each pixel based on a corresponding one of the plurality of generated color scales; and display the generated blood vessel image data, wherein the processing circuitry is further configured to sequentially shift the plurality of color scales in time series so that the blood vessel image data is generated as a moving image in which, for each pixel of the plurality of pixels, the assigned color at the pixel changes periodically, in each frame of the moving image, each pixel of the plurality of pixels in the blood vessel region is assigned a color based on a corresponding one of the plurality of color scales, a color scale period over which each of the color seale scales is defined is a period from an initial time to an ending time during which the concentrations of the contrast agent change, each of the color scales includes multiple repetitions of a component color scale having a period shorter than the color scale period, and each repetition of the component color scale has a same color change pattern, and the component color scale starts with a first color and ends with the first color.

2. The medical image processing apparatus of claim 1, wherein the processing circuitry is further configured to generate the blood vessel image data using the generated plurality of color scales, the blood vessel image data being generated as the moving image in which changes of pixel values different from each other are assigned to the determined times.

3. The medical image processing apparatus of claim 1, wherein the processing circuitry is further configured to generate the blood vessel image data using the plurality of color scales, the blood vessel image data being generated as the moving image in which a frame interval is different from a frame interval of the X-ray contrast image data.

4. The medical image processing apparatus of claim 1, wherein the processing circuitry is further configured to generate the plurality of color scales by assigning a change in a pixel value.

5. The medical image processing apparatus of claim 4, wherein the processing circuitry is further configured to generate the plurality of color scale scales by assigning a pixel value, different from the change in the pixel value.

6. The medical image processing apparatus of claim 4, wherein the processing circuitry is further configured to generate the plurality of color scale scales by assigning a transparency.

7. The medical image processing apparatus of claim 1, wherein the processing circuitry is further configured to generate the blood vessel image data to have, for each pixel, a brightness value according to the concentration of the contrast agent at the specific condition.

8. The medical image processing apparatus of claim 1, wherein the specific condition is maximum values, a predetermined ratio of the maximum values, or a threshold value.

9. The medical image processing apparatus of claim 1, wherein the processing circuitry is further configured to generate the blood vessel image data based on the determined times, which have a data interval shorter than a sampling interval of the concentrations of the contrast agent.

10. The medical image processing apparatus of claim 9, wherein the processing circuitry is further configured to obtain the determined times having the data interval shorter than the sampling interval of the concentrations of the contrast agent, by interpolation processing, curve fitting processing, or gravity center calculation processing.

11. The medical image processing apparatus of claim 1, wherein the processing circuitry is further configured to generate the blood vessel image data based on the determined times, after performing average processing in at least one of spatial directions and the time direction.

12. The medical image processing apparatus of claim 1, wherein the processing circuitry is further configured to generate the blood vessel image data based on the determined times, after low-pass filtering processing in at least one of spatial directions and the time direction.

13. The medical image processing apparatus of claim 1, wherein the processing circuitry is further configured to generate the color seale scales by assigning a continuous change in color phase hue to the determined times.

14. The medical image processing apparatus of claim 1, wherein the processing circuitry is further configured to generate the blood vessel image data for blood vessels by assigning colors to the determined times, which are corresponding arrival times of the contrast agent to the blood vessels.

15. The medical image processing apparatus of claim 1, wherein the moving image has blood vessels where pixel values of pixels in the blood vessels change periodically corresponding to a frame interval of the moving image.

16. The medical image processing apparatus of claim 1, wherein the period of the component color scale is constant and does not vary within the color scale period.

17. The medical image processing apparatus of claim 1, wherein the initial time is an acquisition time of an initial frame of the contrast image data or the DSA image data and the ending time is an acquisition time of an end frame of the contrast image data or the DSA image data.

18. An X-ray diagnostic apparatus, comprising:

an X-ray tube and an X-ray detector configured to acquire X-ray contrast image data from an object; and processing circuitry configured to:

determine, for each pixel of a plurality of pixels in a blood vessel region of two-dimensional projection image data of blood vessels in a head, the two-dimensional projection image data being the X-ray contrast image data acquired in time series or in digital subtraction angiography image data acquired in the time series, a determined time at which a concentration of a contrast agent satisfies a specific condition;

generate a plurality of color scale scales that map a respective color to each of the determined times, the plurality of color scales being respectively different from each other and temporally offset relative to one another:

generate blood vessel image data from the determined times by assigning a color to each pixel based on a corresponding one of the plurality of generated color scale scales; and display the generated blood vessel image data, wherein the processing circuitry is further configured to sequentially switch the plurality of color scales in time series so that the blood vessel image data is generated as a moving image in which, for each pixel of the plurality of pixels, the assigned color at the pixel changes periodically, in each frame of the moving image, each pixel of the plurality of pixels in the blood vessel region is assigned a color based on a corresponding one of the plurality of color scales, a color scale period over which each of the color scales is defined is a period from an initial time to an ending time during which the concentrations of the contrast agent change, each of the color scales includes multiple repetitions of a component color scale having a period shorter than the color scale period, and each repetition of the component color scale has a same color change pattern, and the component color scale starts with a first color and ends with the first color.

19. A medical image processing method, comprising:

determining, for each pixel of a plurality of pixels in a blood vessel region of two-dimensional projection image data of blood vessels in a head, the two-dimensional projection image data being X-ray contrast image data acquired in time series or digital subtraction angiography image data acquired in the time series, a determined time at which a concentration of a contrast agent satisfies a specific condition;

generating a plurality of color scales that map a respective color to each of the determined times, the plurality of color scales being respectively different from each other and temporally offset relative to one another;

generating blood vessel image data from the determined times by assigning a color to each pixel based on a corresponding one of the plurality of generated color scales; and displaying the generated blood vessel image data, wherein the method further comprises sequentially switching the plurality of color scales in time series so that the blood vessel image data is generated as a moving image in which, for each pixel of the plurality of pixels, the assigned color at the pixel changes periodically, in each frame of the moving image, each pixel of the plurality of pixels in the blood vessel region is assigned a color based on a corresponding one of the plurality of color scales, a color scale period over which each of the color scale scales is defined is a period from an initial time to an ending time during which the concentrations of the contrast agent change, and each of the color scales includes multiple repetitions of a component color scale having a period shorter than the color scale period, and each repetition of the component color scale has a same color change pattern, and the component color scale starts with a first color and ends with the first color.

20. An X-ray diagnostic method, comprising:

acquiring X-ray contrast image data from an object;

determining, for each pixel of a plurality of pixels in a blood vessel region of two-dimensional projection image data of blood vessels in a head, the two-dimensional projection image data being the X-ray contrast image data acquired in time series or in digital subtraction angiography image data acquired in the time series, a determined time at which a concentration of a contrast agent satisfies a specific condition;

generating a plurality of color scales that map a respective color to each of the determined times, the plurality of color scales being respectively different from each other and temporally offset relative to one another;

generating blood vessel image data from the determined times by assigning a color to each pixel based on a corresponding one of the plurality of generated color scale scales; and displaying the generated blood vessel image data, wherein the method further comprises sequentially switching the plurality of color scales in time series so that the blood vessel image data is generated as a moving image in which, for each pixel of the plurality of pixels, the assigned color at the pixel changes periodically, in each frame of the moving image, each pixel of the plurality of pixels in the blood vessel region is assigned a color based on a corresponding one of the plurality of color scales, a color scale period over which each of the color scales is defined is a period from an initial time to an ending time during which the concentrations of the contrast agent change, each of the color scales includes multiple repetitions of a component color scale having a period shorter than the color scale period, and each repetition of the component color scale has a same color change pattern, and the component color scale starts with a first color and ends with the first color.

* * * * *